United States Patent [19]

Toja et al.

[11] Patent Number: 4,594,348

[45] Date of Patent: Jun. 10, 1986

[54] USE OF SOME 2-[2-[4-PHENYL-1-PIPERAZINYL]ETHYL]-1H-NAPHTH-[1,2-D]IMIDAZOLE DERIVATIVES AND THEIR PHARMACEUTICALLY ACCEPTABLE SALTS IN THE TREATMENT OF CARDIOVASCULAR DISEASES

[75] Inventors: Emilio Toja; Domenico Barone; Emiliana Baldoli, all of Milan, Italy

[73] Assignee: Gruppo Lepetit S.p.A., Milan, Italy

[21] Appl. No.: 698,653

[22] Filed: Feb. 6, 1985

[30] Foreign Application Priority Data

Feb. 7, 1984 [GB] United Kingdom ............... 8403141

[51] Int. Cl.[4] ........................................... A61K 31/50
[52] U.S. Cl. ................................................. 514/253
[58] Field of Search ...................................... 514/253

[56] References Cited

FOREIGN PATENT DOCUMENTS 0034249 8/1981 European Pat. Off. .

Primary Examiner—Allen J. Robinson

Attorney, Agent, or Firm—William J. Stein; Stephen L. Nesbitt

[57] ABSTRACT

The present invention is directed to a new pharmacological use of some known naphthoimidazole derivatives. More particularly, the compounds of the invention are 2-[2-(4-phenyl-1-piperazinyl)ethyl]-1H-naphtho[1,2-d]imidazoles of formula

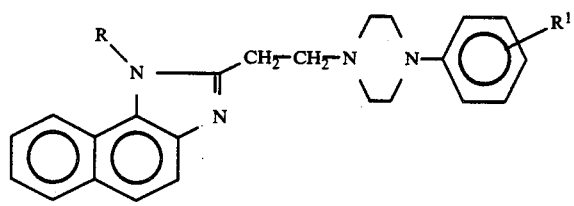

wherein R is selected from methyl and 1-methylethyl and $R^1$ is selected from hydrogen, chloro, methoxy and trifluoromethyl and the pharmaceutically acceptable acid addition salts thereof and possess antihypertensive activity.

3 Claims, No Drawings

USE OF SOME 2-[2-[4-PHENYL-1-PIPERAZINYL]ETHYL]-1H-NAPHTH-[1,2-D]IMIDAZOLE DERIVATIVES AND THEIR PHARMACEUTICALLY ACCEPTABLE SALTS IN THE TREATMENT OF CARDIOVASCULAR DISEASES

The present invention is directed to a new pharmacological use of some known naphthoimidazole derivatives.

A class of naphth[1,2-d]imidazoles and naphth[1,2-d]oxazoles was disclosed in European Patent Application No. 81100152.8—published on Aug. 26, 1981 under Publication No. 0034249—as possessing CNS depressant activity.

Surprisingly, it has been found that a very limited number, among all the compounds therein disclosed, possess an interesting antihypertensive activity. More particularly, the compounds of the invention are 2-[2-(4-phenyl-1-piperazinyl)ethyl]-1H-naphth[1,2-d]imidazoles of formula

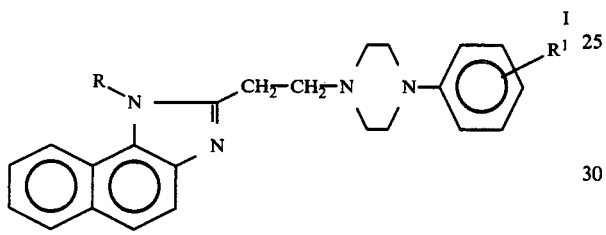

wherein R is selected from methyl and 1-methylethyl and $R^1$ is selected from hydrogen, chloro, methoxy and trifluoromethyl and the pharmaceutically acceptable acid addition salts thereof.

These compounds are prepared as described in the cited European Patent Application, following different known per se methods.

The easiest and most convenient method, according to the prior disclosure, is the nucleophilic displacement on a naphthoimidazole derivative of formula II

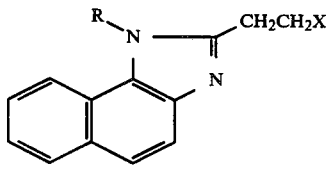

wherein R is as above and X represents a halogen atom, such as a chlorine or bromine, with a suitably selected nucleophile of formula III

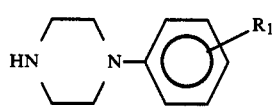

The reaction is carried out by refluxing a solution of the two reactants in a polar organic solvent such as methanol, ethanol, acetonitrile, acetone, or a mixture thereof, and the like, under inert atmosphere for several hours. In order to remove the hydrogen halide which forms during the reaction, a double molar amount of the amine of formula III is preferably employed; alternatively, other basic agents, such as alkali or alkaline earth metal carbonates or organic nitrogen bases such as pyridine, collidine or aliphatic tertiary amines, can be employed. The end products are then recovered by evaporating the solvent and are roughly purified by washing with water. Finally, crystallization from a suitable solvent or column chromatography, or both, gives the purified end-product. Both starting compounds may be employed as free bases or as the corresponding acid addition salts, typically as the hydrochlorides.

The naphthoimidazole derivatives of formula II may be easily prepared from the corresponding diaminonaphthalene derivatives of formula IV

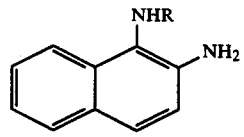

through condensation with a suitably selected acyl chloride of formula

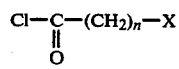

wherein X is as above, followed by cyclization. If desired, the cyclization reaction can be carried out in the presence of at least an equimolar amount of the amine of the above formula III and a hydrogen halide acceptor, as defined before, yielding directly the desired end product.

The diaminonaphthalene derivatives of formula IV are known or may be obtained by reducing the corresponding nitro-compounds of formula V

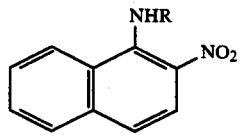

which in turn may be prepared by means of conventional procedures.

A preferred group of compounds of the invention are those of formula I wherein the $R^1$ substituent is in position 3 or 4 of the phenyl ring.

Particularly preferred are those compounds wherein R is as defined, and $R^1$ represents chloro and is in position 4 of the phenyl ring or $R_1$ represents methoxy and trifluoromethyl and is in position 3 of the phenyl ring. Further preferred compounds of the invention are:

2-[2-(4-phenyl-1-piperazinyl)ethyl]-1-(1-methylethyl)-1H-naphth[1,2-d]imidazole, 2-[2-(4-phenyl-1-piperazinyl)ethyl]-1-methyl-1H-naphth-[1,2-d]imidazole, 2-[2-[4-(3-trifluoromethylphenyl)-1-piperazinyl]ethyl]-1-(1-methylethyl)-1H-naphth[1,2-d]-imidazole, 2-[2-[4-(4-chlorophenyl)-1-piperazinyl]ethyl]-1-methyl-1H-naphth[1,2-d]imidazole 2-[2-[4-(3-methoxyphenyl)-1-piperazinyl]ethyl]-1-(1-methylethyl)-1H-naphth[1,2-d]imidazole 2-[2-[4-(3-trifluoromethylphenyl)-1-piperazinyl]ethyl]-1-methyl-1H-naphth[1,2-d]imidazole, 2-[2-[4-(4-chlorophenyl)-1-piperazinyl]ethyl]-1-(1-methylethyl)-1H-naphth[1,2-d]imidazole, and the pharmaceutically acceptable acid addition salts thereof.

Among the usual pharmaceutically acceptable acids, such as those reported in the cited European patent application (No. 81100152), citric acid (i.e. 2-hydroxy-1,2,3-propantricarboxylic acid) is preferred in view of the good solubility and other handling advantages of the final salt.

The most preferred compound of the invention is:
2-[2-[4-(3-trifluoromethylphenyl)-1-piperazinyl]ethyl]-1-(1-methylethyl)-1H-naphth[1,2-d]imidazole, 2-hydroxy-1,2,3-propantricarboxylate.

The following Table lists the names and the chemical formulae of representative compounds of the invention, which are the object of further description in the present patent specification:

hypertensive dogs. Drops in blood pressure are also verified in dogs having a normal blood pressure value.

Experimental models using spontaneously hypertensive non-human animals are widely used in the art to ascertain the antihypertensive activity of new compounds and their potential usefulness in human therapy. It is generally admitted in fact that positive results in animal models are predictive of activity in humans. In particular, experiments using renal hypertensive dogs are described by T. Coleman in "Blood Pressure Control"—Vol. I, (Chapters 5 and 6—Eden Press—MTP press limited—Lancaster, England (1980).

The experiments herein described which use renal hypertensive dogs are conducted essentially as described in the above cited text.

More particularly, in the experiments with conscious

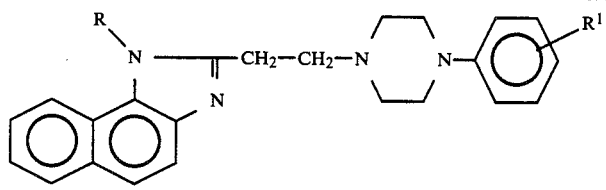

| Compound No. | R | R¹ | Chemical Name |
|---|---|---|---|
| 1 | (CH₃)₂CH | H | 2-[2-[4-phenyl-1-piperazinyl]ethyl]-1-(1-methylethyl)-1H—naphth[1,2-d]imidazole, 2-hydroxy-1,2,3-propantricarboxylate |
| 2 | CH₃ | H | 2-[2-[4-phenyl-1-piperazinyl]ethyl]-1-methyl-1H—naphth[1,2-d]imidazole, 2-hydroxy-1,2,3-propantricarboxylate |
| 3 | (CH₃)₂CH | 3-CF₃ | 2-[2-[4-(3-trifluoromethylphenyl)-1-piperazinyl]ethyl]-1-(1-methylethyl)-1H—naphth[1,2-d]imidazole, 2-hydroxy-1,2,3-propantricarboxylate |
| 4 | CH₃ | 4-Cl | 2-[2-[4-(4-chlorophenyl)-1-piperazinyl]ethyl]-1-methyl-1H—naphth[1,2-d]imidazole |
| 5 | (CH₃)₂CH | 3-OCH₃ | 2-[2-[4-(3-methoxyphenyl)-1-piperazinyl]ethyl]-1-(1-methylethyl)-1H—naphth[1,2-d]imidazole, 2-hydroxy-1,2,3-propantricarboxylate |
| 6 | CH₃ | 3-CF₃ | 2-[2-[4-(3-trifluoromethylphenyl)-1-piperazinyl]ethyl]-1-methyl-1H—naphth[1,2-d]imidazole, 2-hydroxy-1,2,3-propantricarboxylate |
| 7 | (CH₃)₂CH | 4-Cl | 2-[2-[4-(4-chlorophenyl)-1-piperazinyl]ethyl]-1-(1-methylethyl)-1H—naphth[1,2-d]imidazole, 2-hydroxy-1,2,3-propantricarboxylate |

As already said, the compounds of the invention are described in Eur. Pat. Appln. No. 81100152 as possessing CNS activity. This activity was ascertained by means of usual and well-known assays such as the multifactorial observational technique in mice, originally developed by S. Irwin in Psychopharmacologia (Berl.) 13, 222–257 (1968) and modified by C. Morpurgo-Arzneim. Forschung, 21, 1727 (1971) and others.

The parameters evaluated and scored according to the above method are:
a decrease in the spontaneous exploratory activity,
a decrease in the spontaneous locomotory activity,
disturbances in the motor coordination (ataxia)
muscle relaxation Also the conditioned response in rats was evaluated according to the method described by Cook and Weidly in Ann. N.y. Acad. Sci, (1957), 66, 740 and subsequently modified by G. Maffii in Journal Pharm. and Pharmacol. 11, 129–139 (1959).

All the data reported support the view that the described class of compounds possess CNS depressant activity.

Surprisingly, it has been found that the compounds of the present invention are active in animal tests which are considered to be very predictive of antihypertensive activity also in humans.

In particular, the compounds of the invention proved to be capable of lowering the pressure in spontaneously renal hypertensive dogs, mongrel dogs with two clips on the renal arteries were used according to the Goldblatt's method. The compounds were administered by oral route as powder in gelatine capsules. Systolic blood pressure (SBP) was registered at the tail (indirect method).

As for the experiments with conscious normotensive dogs, mongrel dogs with incannulated abdominal aorta or with incannulated abdominal aorta and cardiac left ventricle were used. The compounds were administered by oral route as powder in gelatine capsules. Mean blood pressure (M.B.P.) was registered directly using a Bentley pressure transducer. The results are summarized in the following tables:

TABLE I

| Compound No. | Renal hypertensive dogs | |
|---|---|---|
| | Dose (mg/kg) | % systolic pressure variation |
| 2 | 10 | −32 |
| 3 | 30 | −20 |
|   | 20 | −24 |
| 4 | 20 | −31 |
|   | 10 | −29 |
| 5 | 20 | −20 |
| 6 | 20 | −39 |
| 7 | 5 | −35 |

TABLE I-continued

| Compound No. | Renal hypertensive dogs | |
|---|---|---|
| | Dose (mg/kg) | % systolic pressure variation |
| | 2 | −14 |

TABLE II

| Compound No. | Dose mg/kg | % systolic blood pressure variation |
|---|---|---|
| 1 | 5 | −37 |
| | 1 | −17 |
| 2 | 10 | −30 |
| 3 | 20 | −15 |
| | 10 | −16 |

In addition, compound No. 3 proved to be active in reducing the systolic blood pressure in renal hypertensive dogs when administered orally at a dose as low as 5 mg/kg. This compound proved also to possess a long-lasting activity since the reduction of the blood pressure is still present seven hours after administration. The results of these experiments which were carried out according to the above described technique are summarized in Table III below:

TABLE III

| Dose (mg/kg) | Time (h) | | | | | | | | |
|---|---|---|---|---|---|---|---|---|---|
| | 0 | | 1 | | 3 | | 5 | | 7 | |
| | S.B.P. | % Δ | S.B.P.[a] | % Δ[b] | S.B.P. | % Δ | S.B.P. | % Δ | S.B.P. | % Δ |
| 5 | 210 ± 7 | | 205 ± 5 | −3 | 190 ± 5 | −10 | 185 ± 7 | −12 | 190 ± 4 | −10 |
| 10 | 205 ± 7 | | 190 ± 4 | −8 | 180 ± 7 | −13 | 160 ± 10 | −22 | 170 ± 8 | −18 |
| 20 | 190 ± 8 | | 175 ± 7 | −8 | 165 ± 8 | −14 | 140 ± 7 | −27 | 130 ± 7 | −32 |

[a]S.B.P. = Systolic blood pressure. It is determined after oral administration where three animals were employed for each dose. It is expressed in mmHg as mean value ± SE.
[b]% Δ = % variation of the S.B.P. over the basal value (time 0) at the indicated time after administration.

In the above experiments no increase in the heart rate was observed but only a slight and transient decrease. In another representative experiment compound 3 proved not to induce tachyphylaxis when given per os daily for 7 consecutive days at a dose of 10 mg/kg/die. The results of this experiment are reported in the following Table:

TABLE IV

| | Day of treatment | | | | | | | |
|---|---|---|---|---|---|---|---|---|
| | 1 | | 3 | | 5 | | 7 | |
| | S.B.P.[a] | % Δ[b] | S.B.P | % Δ | S.B.P | % Δ | S.B.P | % Δ |
| Basal value | 210 | | 200 | −5 | 185 | −12 | 180 | −15 |
| peak effect (7h) | 170 | −20 | 170 | −20 | 160 | −24 | 150 | −29 | for the meaning [a] and [b] see Table III above.

During the prolonged treatment no tachycardia or CNS depressant effect was observed.

In a further representative experiment, compound 3 proved not to reduce the myocardial contractility in conscious normotensive dogs.

Myocardial contractility was calculated as $1/P \cdot dp/dt^{(max)}$

The results of this experiment, which was conducted after a single oral administration of 20 mg/kg of the test compound, are summarized below:

TABLE V

| Time (min) | Mean systolic blood pressure (mmHg) | % Δ | Myocardial contractitily (mmHg sec$^{-1}$) | % Δ |
|---|---|---|---|---|
| 0 | 120 | | 48 | |
| 60 | 120 | −0 | 53 | +10 |
| 120 | 106 | −12 | 54 | +12 |
| 180 | 102 | −15 | 53 | +10 |
| 300 | 100 | −17 | 54 | +12 |
| 360 | 106 | −12 | 51 | +6 |

Compound 3 was also tested in the so called "running-fit" test in mice and was found to be inactive at a dose of 30 mg i.p. and 60 mg per os. This test is conducted essentially as described in the literature. The capability of the test compound of antagonizing the effects of the administration of morphine (60 mg/Kg, s.c.) is evaluated by registering and scoring the number of the "run" of the animals in the experiment cage and comparing them with the results of the controls (which do not receive the test compound).

Compound 3 was also found to begin to exhibit its CNS-depressant activity in dogs at a dose which is at least about ten times higher than the effective dose as antihypertensive agent in the same animal species. More particularly, in a representative experiment, mongrel dogs (average weight about 14 kg) orally administered with this compound begin to show some typical signs of CNS-depression (slight sedation and very slight motor incoordination) at 100 mg/kg.

Repeating the same experiment using Beagle dogs (average weight 15 Kg) confirmed that the CNS-depressant effects begins at a dose higher than 100 mg/kg.

The LD$_{50}$ values of the compounds of the invention are generally higher than 500 mg/kg when given per os and generally higher than 200-300 mg/kg when given intraperitoneally to mice. In particular, the approximate LD$_{50}$ values for compound 3 in mice were 1000 mg/kg after oral administration and 600 mg/kg after i.p. administration. In addition, the compounds of the invention proved to be non-mutagenic in in vitro test known to be predictive of tumor-inducing properties. Representative experiments were conducted essentially as described by B. N. Ames, J. McCann., E. Yamasaki, "Methods for detecting carcinogens and mutagens with the salmonella/microsome mutagenicy test" in Mutation Research, 31, 347-364, (1975).

According to the use of the invention the present compounds may be administered in various ways to achieve the desired effect. They may be administered alone or in the form of pharmaceutical preparations to the patient being treated, either orally or parenterally, such as, intraveneously or intramuscularly. The formulation of suitable pharmaceutical compositions can be carried out by the skilled man according to the general common knowledge in the art with the auxilium of reference books such as the "Remington's Pharmaceutical Sciences" Handbook, Mack Publishing Company, U.S.A. The amount of compound administered will vary with the severity of the hypertension, the nature and body weight of the subject of this treatment, the formulation in which the active ingredient is to be administered, the mode of administration, the general health status of the patient, and the interval between each subsequent administration. In consideration of the above parameters, sometimes it may be necessary to deviate from the dosage-range indicated. In general, for oral administration the effective amount of the active compound as antihypertensive is from about 0.035 mg/kg (milligrams per kilograms) of patient body weight per day to about 0.5 mg/kg of patient body weight per day.

For oral administration, a unit dosage may contain, for example, from 0.5 to 20 mg of the active ingredient and preferably from 1 to 10 mg of the active ingredient. Since the compounds of the invention generally possess a long-lasting action, they may be conveniently administered once or twice a day, however, repetitive daily administrations may be, at least in some instances, desirable and will vary with the conditions of the patient and the mode of administration.

As used herein, the term "patient" is taken to mean a warm blooded animal, humans included.

For oral administration the compounds can be formulated into solid or liquid preparations such as capsules, pills, tablets, troches, powders, solutions, suspensions, or emulsions. The solid unit dosage form can be a capsule which can be of the ordinary gelatin type, either hard or soft, containing for example lubricants and inert fillers, such as lactose, sucrose or cornstarch.

In another embodiment of the invention the compounds can be tabletted with conventional tablet-bases such as lactose, sucrose or cornstarch in combination with binders, such as acacia, cornstarch or gelatin, disintegrating agents such as potato starch or alginic acid, and a lubricant such as stearic acid or magnesium stearate.

For parenteral administration the compounds may be administered as injectable doses of a solution or suspension of the compound in a physiologically acceptable diluent with a pharmaceutical carrier which can be a sterile liquid such as water or oils with or without the addition of a surfactant and other pharmaceutically acceptable adjuvants. Examples of oils which can be employed in these preparations are those of mineral petroleum, animal, vegetable or synthetic origin such as peanut oil, soybean oil and mineral oil. In general, water, saline, aqueous dextrose and related sugar solutions, ethanol and glycols such as propylene glycol or polyethylene glycol can be used as liquid carriers for injectable solutions.

The compounds can be administered in the form of a depot injection in such a manner as to permit a sustained release of the active ingredient. The active ingredient can be compressed into pellets or small cylinders and implanted subcutaneously or intramuscularly as depot-injections or implants. Implants may employ inert materials such as biodegradable polymers or synthetic silicones, for example, Silastic ®, a silicone rubber manufactured by the Dow-Corning Corporation. The oral route is generally the preferred route of administration of the compounds of the invention and the capsule is generally the preferred pharmaceutical formulation. One object of the present invention is therefore a method of combatting hypertension in human and non-human animals by administration of an effective dose of a compound of the invention alone or in an admixture with a pharmaceutically acceptable carrier (such as those mentioned above). The term "combatting hypertension" includes the prevention, relief and cure of hypertension.

Another object of the present invention is a pharmaceutical composition for use in combatting hypertension which comprises an antihypertensive amount of a compound of the invention in an admixture with a pharmaceutically acceptable carrier. Also the use of the compounds of the invention for the manufacture of a medicament for combatting hypertension and cardiovascular diseases constitutes a further object of the present invention.

Another object of this invention resides in the present compounds when presented or packaged for use as antihypertensive agents, thus including the pharmaceutical compositions containing an antihypertensive amount of a compound of the invention.

The following are illustrative pharmaceutical formulations which may be employed in practicing the present invention:

A capsule is prepared with:

| | |
|---|---|
| Compound No. 3 | 10 mg |
| Saccharose | 10 mg |
| Polyvinylpyrrolidone | 2 mg |
| Sodium dioctylsulfosuccinate | 0.5 mg |
| Magnesium stearate | 2.5 mg |
| Corn starch | q.s. to 150 mg |

A tablet is prepared with:

| | |
|---|---|
| Compound No. 3 | 10 mg |
| Saccharose | 30 mg |
| Polyvinylpyrrolidone | 5 mg |
| Sodium dioctylsulfosuccinate | 1.4 mg |
| Magnesium stearate | 8 mg |
| Corn starch | q.s. to 250 mg |

Another tablet is prepared with:

| | |
|---|---|
| Active compound | 10 mg |
| Lactose | 102 mg |
| Starch | 27 mg |
| Microcrystalline cellulose | 12 mg |
| Polyvinylpyrrolidone (Mw 25,000) | 12 mg |
| Polysorbate 80 USP | 0.6 mg |
| Magnesium stearate | 0.9 mg |

A sugar coated tablet is prepared with:

| | |
|---|---|
| Compound No. 3 | 5 mg |
| Polyvinylpyrrolidone | 2 mg |
| Sodium carboxymethylcellulose | 1.5 mg |
| Avicel ® | 5 mg |
| Titanium dioxide | 2 mg |

| -continued | |
|---|---|
| Magnesium stearate | 2.5 mg |
| Corn starch | 8 mg |
| Arabic gum | 5 mg |
| Talc | 10 mg |
| Kaolin | 2 mg |
| Saccharose | q.s. to 150 mg |

Soft gelatine capsule with 5 mg of active ingredient

| | |
|---|---|
| Active compound | 5.88 g |
| Glycerol | 24.00 g |
| Polyethylene glycol 400 | 383.32 g |
| Water | 40.00 g |
| | 453.20 g |

The solution is filled into oblong soft gelatine capsules of size 6 minims.

Drops with 4 mg of active compound per ml
The following solution is prepared:

| | For drops with 4 mg per ml |
|---|---|
| Active compound | 4.0 g |
| 96% strength ethanol | 450.0 g |
| Liquid flavouring | 6.0 g |
| Methyl paraben | 1.0 g |
| Polyethylene glycol 400 | 50.0 g |
| 50% strength sugar syrup | 400.0 g |
| Foodstuff colorant (Gelborange S) | 0.6 g |
| Water q.s. to | 1000.0 ml |

The active compound, methyl paraben and flavoring are dissolved at room temperature. Polyethylene glycol 400 and the 50% strength sugar syrup are then slowly added, whilst stirring, the colorant is dissolved and the solution is made up to 1,000 ml with water.

The solution is filled into brown bottles, it also being possible to add sweeteners, if desired.

Syrup with 10 mg of active compound per 10 ml:

| | |
|---|---|
| Active compound | 1.0 g |
| Methyl paraben | 1.0 g |
| 96% strength ethanol | 250.0 g |
| Liquid flavouring | 4.0 g |
| Polyethylene glycol 400 | 100.0 g |
| Glycerol | 250.0 g |
| 50% strength sugar syrup | 300.0 g |
| Foodstuff colorant | 0.5 g |

| -continued | |
|---|---|
| Water q.s. to | 1000.0 g |

It can be prepared essentially as described above in the case of the drops.

We claim:

1. A method of lowering blood pressure in humans which comprises administering to a patient in need thereof an antihypertensive effective amount of a 2-[2-(4-phenyl-1-piperazinyl)ethyl]-1H-naphth[1,2-d]imidazole having the formula

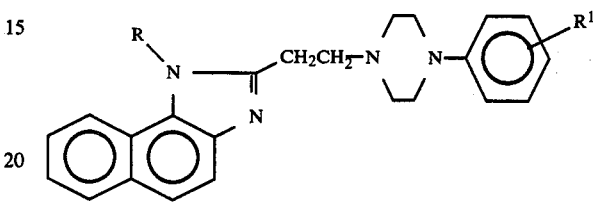

wherein R is methyl or 1-methylethyl; R¹ is selected from the group consisting of hydrogen, chloro, methoxy and trifluoromethyl; or a pharmaceutically acceptable acid addition salt thereof.

2. A method of claim 1 wherein the 2-[2-(4-phenyl-1-piperazinyl)ethyl]-1H-naphth[1,2-d]imidazole is 2-[2-(4-phenyl-1-piperazinyl)ethyl]-1-(1-methylethyl-1H-naphth[1,2-d]imidazole,
2-[2-(4-phenyl-1-piperazinyl)ethyl]-1-methyl-1H-naphth[1,2-d]imidazole,
2-[2-[4-(3-trifluoromethylphenyl)-1-piperazinyl]ethyl]-1-(1-methylethyl)-1H-naphth[1,2-d]imidazole,
2-[2-[4-(4-chlorophenyl)-1-piperazinyl]ethyl]-1-methyl-1H-naphth[1,2-d]imidazole,
2-[2-[4-(3-methoxyphenyl)-1-piperazinyl]ethyl]-1-(1-methylethyl)-1H-naphth[1,2-d]imidazole,
2-[2-[4-(3-trifluoromethylphenyl)-1-piperazinyl]ethyl]-1-methyl-1H-naphth[1,2-d]imidazole,
2-[2-[4-(4-chlorophenyl)-1-piperazinyl]ethyl]-1-(1-methylethyl)-1H-naphth[1,2-d]imidazole,
or a pharmaceutically acceptable acid addition salt thereof.

3. A method of claim 1 wherein the 2-[2-(4-phenyl-1-piperazinyl)ethyl]-1H-naphth[1,2-d]imidazole is 2-[2-[4-(3-trifluoromethylphenyl)-1-piperazinyl]ethyl]-1-(1-methylethyl)-1H-naphth[1,2-d]imidazole, 2-hydroxy-1,2,3-propantricarboxylate.

* * * * *

UNITED STATES PATENT AND TRADEMARK OFFICE
CERTIFICATE OF CORRECTION

PATENT NO. : 4,594,348

DATED : June 10, 1986

INVENTOR(S) : Emilio Toja et al.

It is certified that error appears in the above-identified patent and that said Letters Patent is hereby corrected as shown below:

At column 9, lines 10-11, the omitted phrase --A solution of the following composition is prepared for about 1,000 capsules:-- should be inserted.

Signed and Sealed this

Eighth Day of January, 1991

Attest:

HARRY F. MANBECK, JR.

Attesting Officer

Commissioner of Patents and Trademarks